(12) United States Patent
Yamaki et al.

(10) Patent No.: US 6,878,378 B1
(45) Date of Patent: Apr. 12, 2005

(54) EXTERNAL SKIN CARE COMPOSITION

(75) Inventors: Kazuhiro Yamaki, Tokyo (JP);
Tomohiko Sano, Tokyo (JP); Kimihiko Hori, Ichikai-machi (JP); Yutaka Takagi, Ichikai-machi (JP); Yukihiro Ohashi, Tokyo (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/564,549

(22) Filed: May 4, 2000

(30) Foreign Application Priority Data

May 10, 1999 (JP) .......................................... 11-128255

(51) Int. Cl.[7] .............................. A61K 7/00; A61K 9/14; A61K 7/42; A61K 7/04; A61K 7/021
(52) U.S. Cl. ........................ 424/401; 424/489; 424/59; 424/61; 424/63; 424/64; 424/742
(58) Field of Search ........................... 424/401, 59, 61, 424/63, 64, 489, 742, 54; 514/256

(56) References Cited

U.S. PATENT DOCUMENTS

| | | | | |
|---|---|---|---|---|
| 3,972,997 A | * | 8/1976 | Nakashio et al. | 424/49 |
| 5,157,036 A | * | 10/1992 | Grollier | 514/256 |
| 5,472,698 A | | 12/1995 | Rawlings et al. | 424/401 |
| 5,571,503 A | | 11/1996 | Mausner | 424/59 |
| 5,658,578 A | * | 8/1997 | Ogawa et al. | 424/401 |
| 5,690,947 A | | 11/1997 | Habif et al. | 424/401 |
| 5,747,022 A | * | 5/1998 | Slavtcheff | 424/401 |
| 5,780,047 A | * | 7/1998 | Kamiya et al. | 424/443 |
| 6,224,850 B1 | * | 5/2001 | Breton et al. | 424/47 |
| 6,329,343 B1 | * | 12/2001 | Leung et al. | 514/23 |
| 6,348,200 B1 | * | 2/2002 | Nakajima et al. | 424/401 |

FOREIGN PATENT DOCUMENTS

| | | | | |
|---|---|---|---|---|
| DE | 35 22 572 | | 1/1987 | |
| EP | 0 993 822 A1 | * | 4/2000 | |
| FR | 2 633 515 | | 1/1990 | |
| WO | WO 9714401 | * | 4/1997 | A61K/7/48 |
| WO | WO 98/22084 | * | 5/1998 | |

OTHER PUBLICATIONS

Derwent Publications, AN 1997–115199, JP 9–002952, Jan. 7, 1997.

* cited by examiner

Primary Examiner—Shengjun Wang
(74) Attorney, Agent, or Firm—Oblon, Spivak, McClelland, Maier & Neustadt, P.C.

(57) ABSTRACT

The invention relates to an external skin care composition comprising a ceramide production-accelerating agent and a film-forming polymer. The external skin care composition can enhance the barrier function of the skin and has an excellent skin roughness-improving effect.

8 Claims, 3 Drawing Sheets

CERAMIDO PRODUCTION-ACCELERATING ACTIVITY IN CELL CULTURE SYSTEM

EXTERNAL SKIN CARE COMPOSITION

BACKGROUND OF THE INVENTION

1. Field of the Invention

The present invention relates to an external skin care composition which can enhance the moisturizing function and barrier function of the skin and has an excellent skin roughness-improving effect.

2. Description of the Background Art

Ceramide which is one of sphingolipids is largely present in the horny layer and is known to deeply participates in the development of protecting function and barrier function of the skin to have effects on the improvement of a rough skin and the prevention of cutaneous aging. Therefore, it is attempted to apply an external skin care composition with natural ceramide or pseudoceramide incorporated therein to the skin so as to supply decreased ceramide in the horny layer. According to this attempt, however, no long-term effect is recognized, and stability is insufficient. On the other hand, substances capable of facilitating the synthesis of ceramide in epidermic cells have been found, and it has also been conducted to develop preparations for effectively increasing the amount of ceramide in the horny layer. However, their effects to improve a rough skin have been yet insufficient.

SUMMARY OF THE INVENTION

It is an object of the present invention to provide an external skin care composition which can enhance the barrier function of the skin and has an excellent skin roughness-improving effect.

The present inventors have found that when a ceramide production-accelerating substance and a high-molecular compound having film-forming properties are used in combination, an excellent skin roughness-improving effect is synergistically exhibited.

According to the present invention, there is thus provided an external skin care composition comprising a ceramide production-accelerating agent and a film-forming polymer.

The external skin care composition according to the present invention can enhance the barrier function of the skin and has a marked skin roughness-improving effect.

BRIEF DESCRIPTION OF THE DRAWINGS

The above and other objects, features and advantages of the present invention will become apparent from the following description and the appended claims, taken in conjunction with the accompanying drawings, in which:

DETAILED DESCRIPTION OF THE PREFERRED EMBODIMENTS

Figure 1:
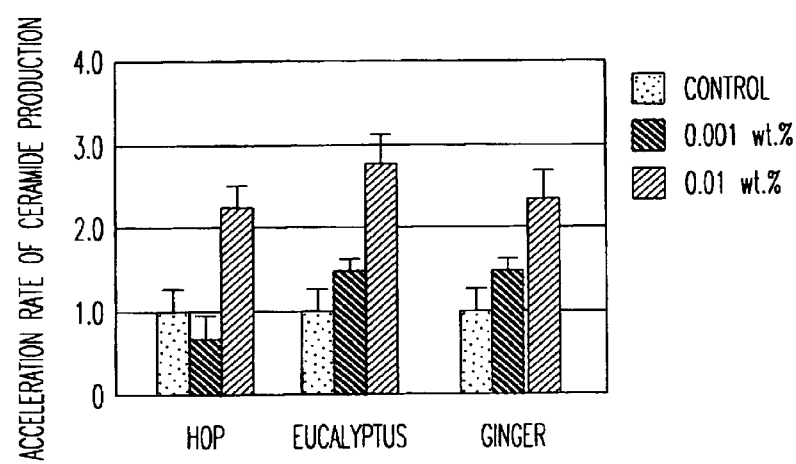
FIG. 1 diagrammatically illustrates the ceramide production-accelerating effects of extracts of *eucalyptus* (*Eucalyptus globulus*), hop and ginger (zingiber) on human keratinocytes.

No particular limitation is imposed on the ceramide production-accelerating substance useful in the practice of the present invention so far as it is a substance capable of accelerating the production of ceramide in the skin. Examples thereof include (1) plants, and extracts, steam distilled products and pressed products thereof, and (2) nicotinic acid, nicotinic acid salts, nicotinyl alcohol and derivatives thereof.

Examples of the plants in the item (1) include *eucalyptus*, hop, zingiber, *Uncaria gambir* Roxburgh, *Rosa multiflora* Thunberg, horse chestnut, lily, Job's-tears, cattail, loquat, cape jasmine, *Panax ginseng* C. A. Meyer, *Saponaria officinalis* Linne, white birch, hydrangea, clove, safflower, Sanguisorba officinalis Linne, iris and *Sophora flavescens* Aiton.

*Eucalyptus* is a plant of *Eucalyptus globulus* or any other related species thereof, belonging to the family Myrtaceas, and its leaves, twigs, blossoms or fruits are mainly used.

Hop (*Humulus lupulus*) is a plant belonging to the family Moraceae, and its female flower spikes are mainly used.

Zingiber (*Zingiberis rhizoma*) is a plant belonging to the family Zingiberaceae, and its rhizome (ginger) is mainly used.

*Uncaria gambir* Roxburgh is a plant belonging to the family Rubiaseae, and its leaves or young branches are mainly used.

*Rosa multiflora* Thunberg is a plant belonging to the family Rosaceae, and its false fruits or fruits (nuts) (i.e., rose fruit) are mainly used.

Horse chestnut (*Aesculus hippocastanum* Linne) is a plant belonging to the family Hippocastanaceae, and its seeds, leaves or bark is mainly used.

Lily (*Lilium candidum*) is a plant belonging to the family Liliaceae, and its bulb is mainly used.

Job's-tears (*Coix lacryma*-jobi Linne var. *ma-yuen* Stapf) is a plant belonging to the family Gramineae, and its seeds (Coicis semen) from which a seed coat has been removed are mainly used.

Cattail is a plant of *Typha angustifolia* linne or any other related species thereof, belonging to the family Typhaceae, and its flower spikes are mainly used Loquat (*Eriobotrya japonica* Lindley) is a plant belonging to the family Rosaceae, and its leaves are mainly used.

Cape jasmine (*Gardenia jasminoides* Ellis) is a plant belonging to the family Rubiaseae, and its fruits are mainly used. *Panax ginseng* C. A. Meyer (*Panax schinseng* Nees) is a plant belonging to the family Araliaceae, and its root or a steamed and dried product thereof is mainly used.

*Saponaria officinalis* Linne is a plant belonging to the family Caryophyllaceae, and its leaves or root is mainly used.

White birch is a plant of *Betula pendula* Roth or any other related species thereof, belonging to the family Betulaceae, and its leaves, bark, xylem or sap is mainly used.

Hydrangea (*Hydrangea serrata* Seringe var. *thunbergii* Sugimoto; *Hydrangea macrophylla* Seringe var. *thunbergii* Makino) is a plant belonging to the family Saxifragaceae, and its leaves or the tips of branches thereof are mainly used.

Clove (*Syzygium aromaticum* Merrill et Perry; *Eugenia caryophyllata* Thunberg) is a plant belonging to the family Myrtaceae, and its spikes (ears), flower stalks, immature fruits or leaves are mainly used.

Safflower (*Carthamus tinctorius* Linne) is a plant belonging to the family Compositae, and its flower, a portion obtained by removing most of a yellow pigment from the flower, or the whole thereof is mainly used.

*Sanguisorba officinalis* Linne is a plant belonging to the family Rosaceae, and its root or rhizome is mainly used.

Iris is a plant belonging to the family Iridaceae, exemplified by *Iris florentina* L., *Iris germania* L., *Iris pallida* L., etc., and its rhizome is mainly used.

*Sophora flavescens* Aiton is a plant belonging to the family Leguminosae, and its root or a portion obtained by removing most of the periderm of the root is mainly used.

In the present invention, the above-described plants may be used as they are, or after they are dried and ground. However, extracts, steam distilled products or pressed products thereof may also be used. More purified products thereof, such as essential oils, may also be used, or commercial products may also be utilized.

Examples of a solvent used in extraction include those routinely used in extraction of plant components, such as water, petroleum ether, n-hexane, toluene, dichloroethane, chloroform, ether, ethyl acetate, acetone, methanol, ethanol, propanol, butanol, ethylene glycol, propylene glycol and butylene glycol. Of these, water, ethanol, propylene glycol and butylene glycol are particularly preferred. These solvents may be used either singly or in any combination thereof. Ordinary conditions may be applied for the extraction. For example, any one of the above-described plants is immersed at 3 to 100° C. for several hours to several weeks in the solvent or heated under reflux. When the plant is used as an essential oil, the conventional method may also be adopted. For example, the essential oil may be obtained from any one of the above-described plants by steam distillation, extraction or pressing. The extracts, steam distilled products or pressed products of these plants may be used as ceramide production-accelerating agents in the present invention as they are. However, a fraction with high activity may also be fractionated by a proper isolating means, for example, gel filtration, chromatography or rectification.

Examples of nicotinic acid (salts), nicotinyl alcohol and derivatives thereof in the item (2) include niconitic acid, methyl nicotinate, ethyl nicotinate, benzyl nicotinate, nicotinamide, nicametate citrate, tocopherol nicotinate, quinolinic acid, pyridine-3,5-dicarboxylic acid, nicotinamide adenine dinucleotide phosphate (NADP), niconitic acid mononucleotide, nicotinyl alcohol and tartaric acid nicotinyl alcohol. These compounds may be used in any form of commercial products, synthetic products and extracts from nature.

These ceramide production-accelerating agents may be used either singly or in any combination thereof. Among the above-mentioned ceramide production-accelerating agents, (1) the plants, and extracts, steam distilled products and pressed products thereof are preferred, with *eucalyptus* extract and ginger extract being particularly preferred. The amount of these ceramide production-accelerating agents to be incorporated into the external skin care composition according to the present invention is preferably 0.00001 to 20% by weight, particularly 0.001 to 10% by weight in terms of solid content. In the case of a bath additive composition, such an amount is preferably used in an amount of at least 0.1 ppb, particularly 1 to 1,000 ppb in a bath.

No particular limitation is imposed on the film-forming polymer useful in the practice of the present invention. Specific examples thereof include the following:

Natural Polymers:
  proteins such as collagen, collagen derivatives and decomposition products of keratin, chitin and derivatives thereof, chitosan and derivatives thereof, gum arabic, guar gum, locust bean gum, xanthan gum, acid hetero-polysaccharides derived from callus of plants belonging to the genus *Polyanthes* L., carrageenan, pullulan, pectin, dextrin, quince (*Cydonia oblonga*), agar, hyaluronic acid, chondroitin sulfate, methyl polyglutamate, ethyl polyglutamate, sodium alginate, potassium alginate, propylene glycol alginate, etc.;

Acrylic Resins:
  polyacrylic acid, poly(methyl acrylate), poly-(ethyl acrylate), poly(butyl acrylate), polyacrylamide, poly (N-isopropylacrylamide), ammonium polyacrylate, sodium polyacrylate), crosslinked sodium polyacrylate, polymethacrylic acid, poly(methyl methacrylate, poly-(ethyl methacrylate), poly(butyl methacrylate), polymethacrylamide, sodium methacrylate, acrylic acid-styrene-ammonium methacrylate copolymers, acrylic acid-styrene copolymers, acrylic acid-methacrylamide copolymers, alkyl acrylate-styrene copolymers, alkyl acrylate copolymers, ethyl acrylate-acrylamide-acrylic acid copolymers, ethyl acrylate-butyl acrylate copolymers, ethyl acrylate-ethyl methacrylate copolymers, ethyl acrylate-methyl methacrylate-acrylic acid copolymers, ethyl acrylate-methyl methacrylate copolymers, ethyl acrylate-methacrylic acid copolymers, octyl acrylate-styrene copolymers, octyl acrylate-vinyl acetate copolymers, hydroxypropyl acrylate-butylaminoethyl methacrylate-acrylic acid acrylamide copolymers, butyl acrylate-ethyl hydroxymethacrylate copolymers, butyl acrylate-hydroxymethacrylic acid copolymers, butyl acrylate-methyl methacrylate copolymers, butyl acrylate-methacrylic acid copolymers, butyl acrylate-vinyl acetate copolymers; methyl acrylate-ethyl acrylate copolymers, methyl acrylate-styrene copolymers, methoxyethyl acrylate-hydroxyethyl acrylate-butyl acrylate copolymers, methoxyethyl acrylate-hydroxyethyl acrylate copolymers, acrylic resin alkanolamines, methacrylic acid-styrene copolymers, methacrylic acid-butyl methacrylate copolymers, methacrylic acid-methyl methacrylate copolymers, methyl methacrylate-butyl acrylate-octyl acrylate copolymers, etc.;

Silicones:
  alkyl-modified silicones, oxazoline-modified silicones, dimethylsiloxane-methylcetyloxysiloxane copolymers, high-molecular methyl polysiloxane, etc.;

Celluloses:
  methyl cellulose, ethyl cellulose, cationized cellulose, carboxymethyl cellulose, hydroxyethyl cellulose, hydroxypropyl cellulose, hydroxypropylmethyl cellulose, etc.;

Alkyd Resins:
  isophthalic acid type alkyd resins, epoxy-modified phthalic acid type alkyd resins, succinic acid type alkyd resins, cyclohexane type alkyd resins, cyclohexene type alkyd resins, phthalic acid type alkyd resins, rosin-modified maleic acid type alkyd resins, etc.;

Carboxyvinyl Polymers:
  carboxyvinyl polymers, alkyl-modified carboxyvinyl polymers and calcium or potassium salts thereof, etc.;
  Olefin-maleic anhydride copolymers and salts thereof:

ethylene-maleic anhydride copolymers isobutylene-sodium maleic anhydride copolymers, etc.; Epoxy resins:

bisphenol A type epoxy resin oleic acid esters, bisphenol A type epoxy resin stearic acid esters, bisphenol A type epoxy resin ricinoleic acid esters, epoxy resin beef tallow fatty acid esters, epoxy resin whale oil fatty acid esters, etc.

Vinypayrrolldone-Based Polymers:

poly(vinyl pyrrolidone), vinylpyrrolidone-styrene copolymers, vinylpyrrolidone-vinyl acetate copolymers, diethyl sulfate vinylpyrrolidone-N,N-dimethylaminoethyl-methacrylic acid copolymers, etc.; Amphoteric polymers:

N-methacryloylethyl-N,N-dimethylammonium-α-N-methylcarboxybetaine-stearyl methacrylate copolymers, N-methacryloylethyl-N,N-dimethylammonium-α-N-methyl-carboxybetaine-butyl methacrylate copolymers, etc.; Synthetic polyelectrolytes:

poly(methacryloyloxyethyltrimethylammonium chloride), etc.; and

Other Polymers:

poly(vinyl methyl ether), vinyl methyl ether-ethyl maleate copolymers, vinyl methyl ether-butyl maleate copolymers, styrene-methylstyrene-indene copolymers, toluenesulfonamide resins, polyamide epichlorohydrin, polyethylene-imine, polyethylene glycol, polyethylene glycol-epichlorohydrin-coconut oil alkylamine-dipropylenetriamine condensates, polyvinyl acetal diester aminoacetate, polyvinyl acetal diethylamino-acetate, poly(dimethylmethylenepieridinium chloride), methoxyethylene-maleic anhydride copolymers, dimethyldiallylammonium chloride-acrylamide copolymers, hydrogenated styrene-methylstyrene-indene copolymers, maleic anhydride-diisobutylene copolymer sodium salts, nylon 6, nylon 6,6, polyethylene, polypropylene, polyisobutylene, polyisoprene, polystyrene, polytetrafluoroethylene, polyvinyl alcohol, polyvinyl butyrate, polyvinyl chloride, vinyl acetate-crotonic acid copolymers, vinyl acetate-styrene copolymers, butadiene-acrylonitrile copolymers, etc.

These polymers may be used either singly or in any combination thereof.

Among the above-mentioned film-forming polymers, mucopolysaccharides, silicones, ionic group-containing polymers, polyvinyl alcohol, polyvinyl pyrrolidone, polyethylene glycol, polyacrylamide and alkyl acrylate copolymers are preferred. As the preferred mucopolysaccharides, silicones and ionic group-containing polymer, examples are chitin and derivatives thereof, xanthan gum, pullulan and acid hetero-polysaccharides derived from callus of plants belonging to the genus *Polyanthes* L., and hyaluronic acid; alkyl-modified silicones, oxazoline-modified silicones and high-molecular methyl polysiloxane; and sodium alginate, potassium alginate, polyacrylic acid, acrylic acid-styrene copolymers, carboxyvinyl polymers, alkyl-modified carboxyvinyl polymers and carboxymethyl cellulose.

The amount of these film-forming polymers to be incorporated into the external skin care composition according to the present invention is preferably 0.001 to 60% by weight, particularly 0.005 to 40% by weight from the viewpoints of the feeling of the resulting external skin care composition upon use and stability.

Various kinds of optional components commonly used may be suitably incorporated in the external skin care compositions according to the present invention. For example, surfactants, oils, sterols, amino acids, moisturizers, powders, ultraviolet absorbents, gelling agents, antiinflammatory agents, antioxidants, pH adjusters and other components.

The external skin care composition according to the present invention may be prepared in any form, such as a solubilization system, emulsification system, powder-dispersed solubilization system, powder-dispersed emulsification system or powder-dispersed oil system, in accordance with a method known per se in the art, and can be used for a make-up cosmetic such as a foundation, powder, lip stick, cheek rouge, eye shadow or nail enamel; or a bath additive composition in the form of tablets, capsules, granules, powder or solution.

The pH of the external skin care composition according to the present invention is preferably adjusted to 2 to 11, particularly 3 to 9.

Preparation Example 1

Preparation of *Eucalyptus* Extract

Leaves of *Eucalyptus globulus* Labillardiere were cut into pieces, and a mixed solvent (20:80; 100 ml) of water and 1,3-butanediol was added to the cut pieces (10 g) to conduct extraction at room temperature for 24 hours while sometimes stirring the mixture. The resultant extract was then filtered, and the filtrate was left at rest for 7 days at 5° C. to age the filtrate, and dregs and precipitate formed were separated by filtration. Water (100 ml) was added to the resultant filtrate, and the mixture was concentrated to about 70 ml at 40° C. under reduced pressure. After this process was repeated 3 times, water and 1,3-butanediol were added in such a manner that the concentration of 1,3-butanediol was adjusted to 80 v/v %, and the whole solution amounted to 100 ml.

Preparation Example 2

Plant extracts shown in Table 1 were prepared in accordance with a method known per se in the art.

TABLE 1

| Plant extract | Plant | Extraction solvent |
| --- | --- | --- |
| Hop extract | Female spikes of *Humulus lupulus* | 1,3-Butanediol |
| Ginger extract | Rhizome of *Zingiber officinale* Roscoe | Water:ethanol = 50:50 |
| Gambier extract | Leaves or young branches of *Uncaria gambir* Roxburgh | Water → water:ethanol = 50:50 |
| Rose fruit extract | Fruits of *Rosa multiflora* Thunberg | Water:ethanol = 50:50 |
| Marronnier extract | Seeds of *Aesculus hippocastanum* Linne | Water:1,3-butanediol = 50:50 |
| Lily extract | Bulb of *Lilum candidum*) | Water:1,3-butanediol = 50:50 |

TABLE 1-continued

| Plant extract | Plant | Extraction solvent |
| --- | --- | --- |
| Coicis semen extract | Seeds of *Coix lacryma-jobi* Linne var. *ma-yuen* Stapf from which a seed coat has been removed | Water:1,3-butanediol = 50:50 |
| Cattail extract | Flower spikes of *Typha angustifolia* linne | Water:1,3-butanediol = 10:90 |
| Loquat leaf extract | Leaves of *Eriobotrya japonica* Lindley | Water:1,3-butanediol = 10:90 |
| Cape jasmine extract | Fruits of *Gardenia jasminoides* Ellis | 1,3-butanediol |
| Ginseng extract | Root of *Panax ginseng* C. A. Meyer | Water:ethanol = 50:50 |
| *Saponaria officinalis* Linne extract | Leaves of *Saponaria officinalis* Linne | Water:1,3-butanediol = 50:50 |
| White birch extract | Bark or xylem of *Betula pendula* Roth | Water:ethanol = 50:50 |
| Hydrangea extract | Leaves or branch tips of *Hydrangea serrata* Seringe var. *thunbergii* Sugimoto | Water:ethanol = 50:50 |
| Clove extract | Spikes (ears) of *Syzygium aromaticum* Merrill et Perry | Water:ethanol = 50:50 |
| Safflower extract | The whole *Carthamus tinctorius* Linne | Water:ethanol = 50:50 |
| *Sanguisorba officinalis* Linne extract | Root or rhizome or *Sanguisorba officinalis* Linne | Water:ethanol = 50:50 |
| Iris root extract | Rhizome of *Iris florentia* L. | ethanol |
| *Sophora flavescens* Aiton extract | Root of *Sophora flavescens* Aiton | Water:ethanol:1,3-butanediol = 50:30:20 |

Test Example 1

Test for Acceleration of Ceramide Production (Cell System)

<Method>

Human keratinocytes (HK-f: product of Kyokuto Seiyaku Kogyo K. K.) were cultured for 24 hours at 37° C. under 5% $CO_2$ in a medium (GIBCO SFM/-BPE, EGF) containing [$^{14}$]-serine (product of Daiichi Pure Chemicals Co., Ltd.) using a 6-well plate. The crude drug extract of *eucalyptus*, hop or ginger obtained in Preparation Example 1 or 2 was then added to the medium in a proportion of 0.001% by weight or 0.01% by weight in terms of solid content to conduct the culture for additional 24 hours. After the medium was removed, and the wells were washed once with PBS, cells were scraped with a cell scraper to collect them in a test tube. After water (3.6 ml), chloroform (4 ml) and methanol (4 ml) were added to the human keratinocytes in this test tube to mix them, a chloroform layer was isolated and dried to solid. The lipid extracted was developed to the top twice with a solvent 1 (chloroform:methanol:acetic acid=190:9:1) and to 3 cm from the bottom with a solvent 2 (chloroform:methanol:acetone=76:20:4) on a HPTLC plate [silica gel G60 (20×10 cm), Art. 5641; product of Merck Co.]. The counts of ceramlde and glycosylceramide on the TLC plate were measured by means of an autoradiograph (BAS2000; manufactured by Fuji Photo Film Co., Ltd.).

<Results>

The results obtained by calculating out an acceleration rate of ceramide production with the acceleration rate of a control, to which no crude drug extract was added, regarded as 1.0 are shown in FIG. 1. As apparent from FIG. 1, all extracts of *eucalyptus*, hop and ginger were observed having a ceramide production-accelerating effect on human keratinocytes.

Test Example 2

Test for Acceleration of Ceramide Production (Animal System)

<Method>

The plant extract (0.1% by weight, 0.01% by weight or 0.001% by weight in terms of solid content) of *eucalyptus*, hop or ginger obtained in Preparation Example 1 or 2, which had been diluted with a 7:3 mixed solvent of propylene glycol and ethanol, was applied to the back of a hairless mouse SKHI for 2 weeks, and the skin was then cut out of the back. The skin was subjected to a heat treatment at 60° C. for 60 seconds, thereby peeling the epidermis from the skin. The epidermis was divided into halves, and the horny layer was prepared from one of them using 0.5% trypsin. After the epidermis and horny layer were lyophilized, and their weights were measured, lipid extraction was conducted in accordance with the Bligh/Dyer method (chloroform:methanol:water=4:4:3.6), and the extracts were subjected to HPTLC in the same manner as in Test Example 1. After development, the plate was immersed in a solution containing 8% by weight of phosphoric acid and 10% by weight of copper sulfate to conduct printing at 160° C. for 15 minutes, and ceramide was then determined by means of a densitometer (Bio•Image; manufactured by Bio-Image Co.).

<Results>

Figure 2A:
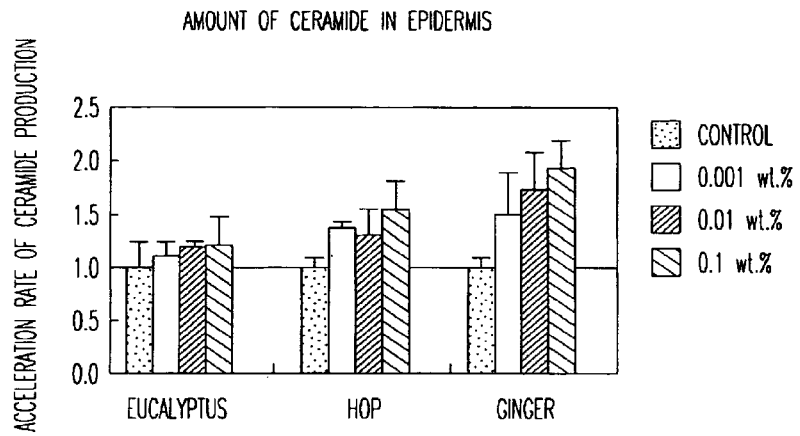
FIG. 2 diagrammatically illustrates the effects of increasing the amount of ceramide in the epidermis and horny layer by the extracts of *eucalyptus* (*Eucalyptus globulus*), hop and ginger (zingiber)
Figure 2B:
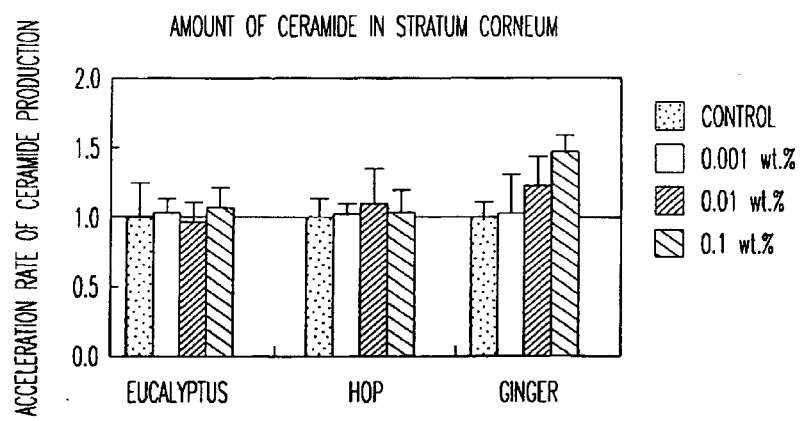

The results obtained by calculating out a quantitative proportion of ceramide with the amount of ceramide in a control, to which no crude drug extract was added, regarded as 1.0 are shown in FIG. 2. As apparent from FIG. 2, all extracts of *eucalyptus*, hop and ginger were observed having an effect of increasing the amounts of ceramide in the epidermis and horny layer.

Test Example 3

Test for Acceleration of Ceramide Production (Cell System)

<Method>

A test for acceleration of ceramide production was conducted in the same manner as in Test Example 1 except that the extracts of gambier, rose fruit, *marronnier*, lily, *Coicis semen*, cattail, loquat, cape jasmine, ginseng, *Saponaria officinalis* Linne, white birch, hydrangea, clove, safflower, *Sanguisorba officinalis* Linne, iris root and *Sophora flavescens* Aiton obtained in Preparation Example 2 were separately used.

<Results>

Figure 3:
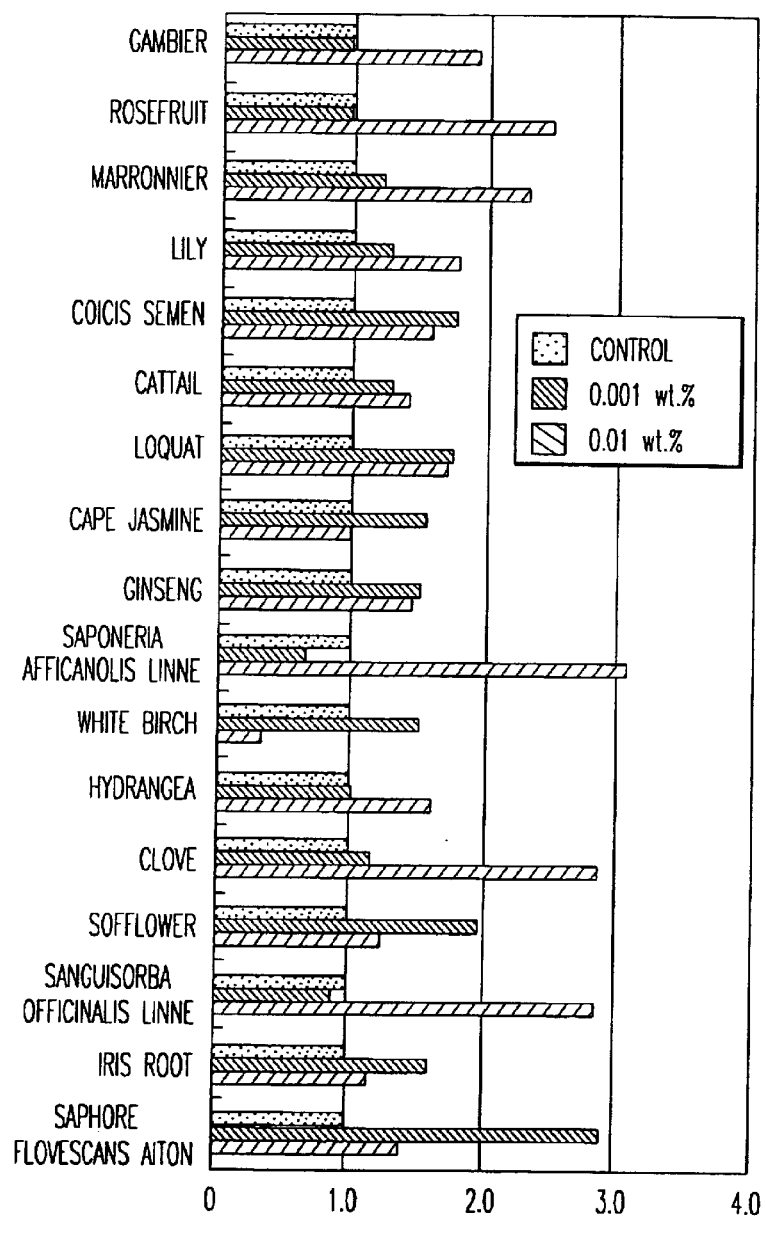
FIG. 3 diagrammatically illustrates the ceramide production-accelerating effects of extracts of gambier (*Uncaria gambir* Roxburgh), rose fruit (*Rosa multiflora* Thunberg), marronnier (horse chestnut), lily, *Coicis semen* (Job's-tears), cattail (*Typha angustifolia* linne), loquat, cape jasmine, ginseng (*Panax ginseng* C. A. Meyer), *Saponaria officinalis* Linne, white birch (*Betula pendula* Roth), hydrangea, clove, safflower, *Sanguisorba officinalis* Linne, iris (*Iris florentina* L.) and *Sophora flavescens* Aiton on human keratinocytes.

The results obtained by calculating out an acceleration rate of ceramide production with the acceleration rate of a control, to which no crude drug extract was added, regarded as 1.0 are shown in FIG. 3. As apparent from FIG. 3, all the extracts were observed having a ceramide production-accelerating effect on human keratinocytes.

Test Example 4

(Examples 1 to 4 and Comparative Examples 1 to 4)

Emulsification type cosmetic compositions having their corresponding formulations shown in Table 2 were prepared in a method known per se in the art to evaluate them as to effects of enhancing the moisturizing function and barrier function of the skin and the improvement rate of skin roughness.

(Evaluation Method)

Chosen as volunteers in winter were 10 women of 20 to 40 years of old who had skin roughness on their both cheeks. Each of the above-prepared external skin care preparations was applied to the left and right cheeks of each volunteer 3 times a day. On the following day of the completion of the 3-week application test, evaluation was made with respect to the following items. The results are shown in Table 2.

(1) Effect of Enhancing a Moisturizing Function:

After washing the face with warm water of 37° C., each volunteer was allowed to rest for 30 minutes in a room which was air-conditioned at 200 and 40% humidity. The water content of her horny layer was then measured by an impedance meter (manufactured by IBS Company). The measured value was indicated by an average value±standard error. A higher measured value indicates that the test sample has a higher effect for enhancing the moisturizing function of the skin.

(2) Effect of Enhancing the Barrier Function of the Skin:

A transepidermal water loss (TEWL) was measured by means of a Hydrometer (manufactured by Meeco Co.) in accordance with a method known per se in the art. A lower transepidermal water loss indicates that the test sample has a higher effect for enhancing the water-retaining function and barrier function of the skin.

(3) Improvement Rate of Skin Roughness:

Skin roughness was observed visually and ranked in accordance with the following standard. Each score was indicated by an average value±standard error. A lower score indicates a higher improvement rate of skin roughness.

0: No skin roughness was observed;

1: Slight skin roughness was observed;

2: Skin roughness was observed;

3: Rather severe skin roughness was observed;

4: Severe skin roughness was observed.

Test Example 5

Emulsification type cosmetic compositions were prepared in the same manner as in Test Example 4 except that extracts of hop, gambler, rose fruit, *marronnier*, lily, *Coicis semen*, cattail, loquat leaf, cape jasmine, ginseng, *Saponaria officinalis* Linne, white birch, hydrangea, clove, safflower, *Sanguisorba officinalis* Linne, iris root and *Sophora flavescens* Aiton set forth in Table 1 were separately incorporated in place of the *eucalyptus* extract in the formulation of Test Example 4 shown in Table 2, and evaluated as to effects of enhancing the moisturizing function and barrier function of the skin and the improvement rate of skin roughness in the same manner as in Test Example 4. As a result, all the emulsification type cosmetic compositions were found to have excellent effects.

Example 5

Toilet lotion

A toilet lotion having the following composition was prepared in accordance with a method known per se in the art.

|  | (wt. %) |
|---|---|
| Eucalyptus extract (in terms of solids) | 0.01 |
| Polyethylene glycol *1 | 1.00 |
| Polyoxyethylene (29) sorbitan monolaurate | 1.50 |
| Glycerol | 2.00 |
| Paraben | 0.10 |
| Purified water | Balance |

*1 PEG-1540, product of Sanyo Chemical Industries, Ltd.

TABLE 2

|  | Example | | | | Comparative Example | | | |
|---|---|---|---|---|---|---|---|---|
|  | 1 | 2 | 3 | 4 | 1 | 2 | 3 | 4 |
| Eucalyptus extract (in terms of solids) | 0.01 | 0.02 | 0.02 | — | — | 0.01 | — | — |
| Ginger extract (in terms of solids) | — | — | — | 0.02 | — | — | — | — |
| Pullulan | 2.0 | 2.0 | 1.0 | — | — | — | 2.0 | 2.0 |
| Polyethylene glycol*1 | — | — | 1.0 | — | — | — | — | — |
| Alkyl acrylate copolymer*2 | — | — | — | 1.0 | — | — | — | — |
| Polyvinyl pyrrolidone*3 | — | — | — | 1.2 | — | — | — | — |
| Cholesterol | — | — | — | — | — | — | — | 0.5 |
| Hydrogenated, purified soybean lecithin | — | — | — | — | — | — | — | 1.0 |
| Sorbitan monostearate | 2.0 | 2.0 | 2.0 | 2.0 | 2.0 | 2.0 | 2.0 | 2.0 |
| 2-Octyldodecyl myristate | 10.0 | 10.0 | 10.0 | 10.0 | 10.0 | 10.0 | 10.0 | 10.0 |
| Squalane | 5.0 | 5.0 | 5.0 | 5.0 | 5.0 | 5.0 | 5.0 | 5.0 |
| succinic acid | 1.0 | 1.0 | 1.0 | 1.0 | 1.0 | 1.0 | 1.0 | 1.0 |
| Potassium succinate trihydrate | 1.0 | 1.0 | 1.0 | 1.0 | 1.0 | 1.0 | 1.0 | 1.0 |
| Purified water | Bal. | Bal. | Bal. | Bal. | Bal. | Bal. | Bal. | Bal. |
| Water content in the horny layer ($\mu$moh) | 25.5 ± 3.3 | 27.0 ± 2.9 | 23.6 ± 2.6 | 27.5 ± 2.5 | 7.2 ± 1.0 | 8.5 ± 0.6 | 9.0 ± 1.0 | 9.5 ± 1.0 |
| Transepidermal water loss (g/m$^2$ · hr) | 7 | 5 | 5 | 4 | 25 | 22 | 20 | 21 |
| Score of skin roughness | 0.9 ± 0.3 | 0.9 ± 0.2 | 0.8 ± 0.2 | 0.7 ± 0.2 | 3.0 ± 0.4 | 2.8 ± 0.8 | 2.4 ± 0.3 | 2.4 ± 0.3 |

*1 PEG-1540, product of Sanyo Chemical Industries, Ltd.
*2 Iodosol GH810, product of Kanebo NSC Ltd.
*3 Rubisquall K-90, product of BASF Japan Ltd.

Example 6

O/W type emulsion An O/W type emulsion having the following composition was prepared in accordance with a method known per se in the art.

| | (wt. %) |
|---|---|
| Eucalyptus extract (in terms of solids) | 0.02 |
| Polyethylene glycol *1 | 1.00 |
| Pullulan *2 | 0.40 |
| Cetyl alcohol | 1.00 |
| Vaseline | 2.00 |
| Squalane | 6.00 |
| Dimethyl polysiloxane | 2.00 |
| Glycerol | 2.00 |
| Pseudoceramide *3 | 1.00 |
| Polyoxyethylene (10) monooleate | 1.00 |
| Glycerol monostearate | 1.00 |
| Acid hetero-polysaccharide derived from callus of plant *4 | 2.00 |
| Paraben | 0.20 |
| Purified water | Balance |

*1 PEG-2000, product of Sanyo Chemical Industries, Ltd.
*2 Pullulan PI-20, product of Hayashibara Company, Ltd.
*3 N-(3-Hexadecyloxy-2-hydroxypropyl)-N-2-hydroxyethylhexadecanamide.
*4 1% by weight aqueous solution of tuberose polysaccharide.

Example 7

W/O type cream A W/O type cream having the following composition was prepared in accordance with a method known per se in the art.

| | (wt. %) |
|---|---|
| Eucalyptus extract (in terms of solids) | 0.02 |
| Alkyl acrylate copolymer *1 | 1.30 |
| polyvinyl pyrrolidone *2 | 0.70 |
| Dimethyl polysiloxane | 10.00 |
| Methylphenyl polysiloxane | 3.00 |
| Octamethylcyclotetrasiloxane | 12.00 |
| Polyoxyalkylene-modified silicone | 5.00 |
| 1-3-Butylene glycol | 6.00 |
| Pseudoceramide *3 | 1.20 |
| Paraben | 0.20 |
| Perfume base | Trace amount |
| Purified water | Balance |

*1 Iodosol GH810, product of Kanebo NSC Ltd.
*2 Rubisquall K-90, product of BASF Japan Ltd.
*3 N-(3-Hexadecyloxy-2-hydroxypropyl)-N-2-hydroxyethylhexadecanamide.

Example 8

Sunscreen composition A sunscreen composition having the following composition was prepared in accordance with a method known per se in the art.

| | (wt. %) |
|---|---|
| Ginger extract (in terms of solids) | 0.01 |
| Alkyl acrylate copolymer *1 | 0.80 |
| Polyethylene glycol *2 | 1.00 |
| Octyl p-methoxycinnamate | 5.00 |
| Silicon-coated zinc oxide | 6.00 |
| Silicon-coated titanium oxide | 0.50 |
| Dimethyl polysiloxane | 5.00 |
| Octamethylcyclotetrasiloxane | 20.00 |
| Polyoxyalkylene-modified silicone | 3.00 |
| Ethanol | 3.00 |
| Glycerol | 3.00 |
| Magnesium sulfate | 1.00 |
| Paraben | 0.20 |
| Perfume base | Trace amount |
| Purified water | Balance |

*1 Iodosol GH810, product of Kanebo NSC Ltd.
*2 PEG-4000S, product of Sanyo Chemical Industries, Ltd.

Example 9

Cosmetic jelly A cosmetic jelly having the following composition was prepared in accordance with a method known per se in the art.

| | (wt. %) |
|---|---|
| Ginger extract (in terms of solids) | 0.01 |
| Polyethylene glycol *2 | 0.50 |
| Xanthan gum *2 | 0.20 |
| Glycerol | 3.00 |
| Ethanol | 3.00 |
| Carboxyvinyl polymer | 0.50 |
| Potassium hydroxide | 0.15 |
| Polyoxyethylene hardened castor oil | 1.00 |
| Citric acid | 0.80 |
| Trisodium citrate | 0.80 |
| Nylon powder | 1.00 |
| Paraben | 0.10 |
| Perfume base | Trace amount |
| Purified water | Balance |

*1 PEG-2000, product of Sanyo Chemical Industries, Ltd.
*2 Neosoft XKK, product of Kohjin Co., Ltd.

Example 10

Liquid bath additive composition A liquid bath additive composition having the following composition was prepared in accordance with a method known per se in the art.

| | (wt. %) |
|---|---|
| Eucalyptus extract (in terms of solids) | 0.02 |
| Pseudoceramide *1 | 0.10 |
| Isopropyl myristate | 15.00 |
| Liquid paraffin | Balance |
| Polyoxyethylene (12) oleyl ether | 10.00 |
| Polyoxyethylene (6) oleyl ether | 6.00 |
| Acid hetero-polysaccharide derived from callus of plant *2 | 2.00 |
| Paraben | 0.30 |
| Perfume base | Trace amount |

*1 N-(3-Hexadecyloxy-2-hydroxypropyl)-N-2-hydroxyethylhexadecanamide.
*2 1% by weight aqueous solution of tuberose polysaccharide.

The present application claims priority from JP 11-128255 filed May 10, 1999.

What is claimed is:

1. An external skin care composition comprising a ceramide production-accelerating agent and a film forming polymer, wherein the ceramide production-accelerating agent is *eucalyptus* extract and the film forming polymer is pullulan.

2. The external skin care composition of claim 1, wherein the film-forming polymer is present in an amount of 0.001 to 60% by weight.

3. The external skin care composition of claim 1, wherein the film-forming polymer is present in an amount of 0.005 to 40% by weight.

4. The external skin care composition of claim 1, wherein the composition further comprises at least one surfactant, oil, sterol, amino acid, moisturizer, powder, ultraviolet absorbent, gelling agent, antiinflammatory agent, antioxidant, or pH adjuster.

5. A cosmetic comprising the composition of claim 1.

6. The cosmetic of claim 5, wherein said cosmetic is selected from the group consisting of a foundation, a powder, a lip stick, a cheek rouge, an eye shadow, a nail enamel, and a bath additive.

7. The external skin care composition of claim 1, wherein the composition has a pH of 2 to 11.

8. The external skin care composition of claim 1, wherein the composition has a pH of 3 to 9.

* * * * *